United States Patent [19]

Ishii et al.

[11] 4,165,296

[45] Aug. 21, 1979

[54] METHOD FOR REGENERATING AN OXIDATION CATALYST

[75] Inventors: Hiromichi Ishii; Hideo Matsuzawa; Masao Kobayashi, all of Otake; Masaaki Kato, Yamaguchi, all of Japan

[73] Assignee: Mitsubishi Rayon Co., Ltd., Tokyo, Japan

[21] Appl. No.: 887,802

[22] Filed: Mar. 17, 1978

[51] Int. Cl.$^2$ .................. B01J 27/28; B01J 23/92; C07C 51/24; C07C 45/02
[52] U.S. Cl. ..................... 252/412; 252/416; 260/604 R; 562/545
[58] Field of Search ................. 252/412, 416; 260/530 N, 533 N, 603 C, 604 R; 562/545

[56] References Cited

U.S. PATENT DOCUMENTS

| | | | |
|---|---|---|---|
| 1,678,626 | 7/1928 | Jaeger et al. | 252/412 |
| 2,683,122 | 7/1954 | Woodcock et al. | 252/412 |
| 2,973,326 | 2/1961 | Hodgins et al. | 252/412 |
| 3,538,017 | 11/1970 | Aglietti et al. | 252/412 |
| 3,761,516 | 9/1973 | Khoobiar | 260/530 N |
| 4,075,244 | 2/1978 | Akiyama et al. | 260/530 N |

*Primary Examiner*—P. E. Konopka
*Attorney, Agent, or Firm*—Oblon, Fisher, Spivak, McClelland & Maier

[57] ABSTRACT

A phosphorus-molybdenum-alkali metal-containing catalyst for the gas-phase oxidation of an unsaturated aldehyde to an unsaturated carboxylic acid is regenerated by treating it with an aqueous solution containing ammonia and hydrogen peroxide or ozone.

7 Claims, No Drawings

METHOD FOR REGENERATING AN OXIDATION CATALYST

BACKGROUND OF THE INVENTION

1. Field of the Invention

This invention relates to methods for regenerating catalysts and, more particularly, to a method for regenerating an oxidation catalyst used in preparing unsaturated aldehydes or acids from the corresponding olefins or aldehydes by gas-phase oxidation.

2. Description of the Prior Art

Oxidation catalysts which are used for producing an unsaturated aldehyde or unsaturated acid from the corresponding olefin or aldehyde by gas-phase catalytic oxidation often lose their activity in use for various reasons such as abnormal reactions, change of structure during a lengthy reaction period, etc.

Such catalysts can also lose their activity if the temperature of the heat treatment before use is too high.

A phosphorus-molybdenum-alkali metal catalyst which can be used in the present invention is disclosed by the present inventors in Japanese Published Unexamined Patent Applications Nos. 41811/75, 142510/75 and 100019/75. This catalyst has excellent performance in the production of unsaturated carboxylic acids from unsaturated aldehydes, but it can lose its activity for the reasons mentioned above.

Such a deactivated catalyst is generally regenerated indirectly by separating and recombining its constituents by a chemical process, but this procedure is very uneconomical from an industrial point of view.

For directly regenerating the deactivated catalyst, various methods are known. For example, a catalyst containing phosphorus and vanadium is regenerated by treatment with halogen or halide as disclosed in Belgian Pat. No. 846,608; a catalyst containing phosphorus and molybdenum is regenerated by treatment with aqueous ammonia as described in Japanese Published Examined Patent No. 33082/72; a molybdenum-bismuth catalyst is regenerated by treatment with aqueous ammonia as described in Japanese Published Examined Patent No. 27751/68; and a molybdenum-vanadium-arsenic catalyst is regenerated by treatment with aqueous ammonia as disclosed in Japanese Published Examined Patent No. 23615/70. However, the cataysts regenerated by these methods are still insufficient in performance and therefore, a need continues to exist for a more effective regenerating method.

SUMMARY OF THE INVENTION

Accordingly, it is an object of this invention to provide a method for regenerating an oxidation catalyst.

A further object is to provide an improved method for regenerating a phosphorus-molybdenum-alkali metal-containing oxidation catalyst. A further object is to provide an economical method for regenerating a phosphorus-molybdenum-alkali metal oxidation catalyst.

Accordingly, the inventors conducted an extensive study of regenerating methods for phosphorus-molybdenum-alkali metal-containing catalysts which have become inactive for various reasons, with the goal of regenerating the catalyst to its original performance, economically from an industrial point of view. They have found that such a catalyst can be regenerated to a highly active state by treatment with aqueous ammonia and hydrogen peroxide solution or aqueous ammonia and ozone. Subsequently, the aqueous solvent is evaporated, the solid recovered, dried and calcined in air.

DETAILED DESCRIPTION OF THE PREFERRED EMBODIMENTS

The catalyst to be regenerated by the present invention is an oxidation catalyst containing phosphorus, molybdenum and alkali metal. The preferable atomic proportions of phosphorus and the metal elements are 0.5–6 of phosphorus, 0.2–6 of alkali metal in total, and, if desired, 0.01–12 of optional metal component in total, and 12 of Mo, respectively.

As the alkali metal, potassium, rubidium and cesium are especially preferable.

As the metal to be added is as an optional component, As, SB, Cd, In, Sn, Tl, Ca, V, U, Ce, W, Ni, Zr, Ca, Ba, Fe, Rh, Mn, Re, Ru, Co, Cu, Al, Si, Cr, Ge, Ti, Nb, Ta, Pb, Zn, Sr, Mg, Ga, Pd, B, Bi, Te and Ag are suitable.

When a catalyst containing the above-mentioned metals is used to produce an unsaturated acid by the catalytic oxidation of an unsaturated aldehyde in the vapor phase, the catalyst often loses its activity because of the various problems mentioned above, which are encountered in industrial production. Such an inactivated catalyst can be effectively regenerated by the method of this invention.

The regeneration according to this invention is carried out in aqueous medium using 1–50 parts of ammonia and 1–50 parts by weight of oxidizing agent per 100 parts of deactivated catalyst. The ammonia is conveniently added as an aqueous ammonia solution. The oxidizing agent used must be a strong oxidizing agent. Hydrogen peroxide and ozone are preferred. Air, on the other hand, is too weak an oxidizing agent to produce a good regeneration.

It is preferred to carry out the regeneration in the presence of up to 26 parts of a source of nitrate ion per 100 parts of deactivated cataysyt. Preferred sources of nitrate ion are nitric acid and ammonium nitrate.

The regeneration temperature is not critical, although elevated temperatures up to the boiling point of the solution at the prevailing pressure may be employed. If low temperatures are used, the reaction time will be increased while at elevated temperatures, it will be shorter. Temperatures of from 20° C. to 100° C. have been found suitable.

After the regeneration is complete the regenerated catalyst is recovered by evaporating the solution to dryness and thoroughly drying the solid residue. The dried catalyst is then finely ground, compression molded to the form desired for the catalytic reaction, and calcined in air. The conditions are essentially the same as those employed originally to prepare the original catalyst.

In carrying out the regeneration reaction, the deactivated catalyst is suspended in water and the required amount of aqueous ammonia and optionally the nitrate ion source are added with stirring. The catalyst may or may not dissolve in the regenerating solution, but this does not affect the regeneration reaction. Then the oxidizing agent is added gradually while agitation is continued. Hydrogen peroxide may be added slowly, e.g., dropwise, as an aqueous solution, while ozone may be bubbled through the reaction mixture. Subsequently, the reaction mixture is evaporated to dryness and the solid residue is dried in an oven. The dried catalyst is then pulverized, compression molded, and calcined in air.

The presence of nitrate ion during the regeneration process increases the effect of the regeneration. This is thought to be due to nitrate ion combining with ammonium ion to form ammonium nitrate which is removed during the calcining treatment, thus changing the distribution and volume of the pores in the catalyst.

When the regenerated catayst prepared by the process of this invention is analyzed by powder X-ray diffraction, a sharp diffraction line characteristic of a phosphorus-molybdenum-alkali metal complex compound can be observed and the diffraction pattern of a molybdenum oxide such as molybdenum trioxide, which is observed in the deactivated catalyst, disappears. In other words, the regenerated catalyst produce the same powder X-ray diffraction pattern as a highly active catalyst does.

Furthermore, when the regenerated catalyst is used for producing methacrylic acid from methacrolein, nearly the same results are obtained as with a highly active catalyst before inactivation.

The catalyst regenerated by the process of this invention may be used to oxidize an unsaturated aldehyde such as acrolein or methacrolein, to the corresponding carboxylic acid with oxygen in the gase phase.

Usually, the reactants are diluted with an inert gas such as nitrogen, steam or carbon dioxide and then passed over the catalyst. The presence of steam, especially, may increase the yield of unsaturated acid.

The reaction is preferably conducted at normal pressure. However, it may be conducted at slightly reduced or increased pressure, for example, 0.5–20 atms (absolute).

The proportions of unsaturated aldehyde and oxygen when the gas-phase catalytic oxidation of unsaturated aldehyde is carried out using the regenerated catalyst can be varied over a wide range, but it is preferable to maintain the unsaturated aldehyde and oxygen in the range of 1–20%, respectively, and the inert gas in the range of 60–98%.

The following general procedure may be used in carrying out the regeneration of a deactivated phosphorus-molybdenum-alkali metal-containing oxidation catalyst by the process of this invention: 100 Parts by weight of deactivated catalyst and 0–26 parts by weight of a nitrate ion source are added to pure water, 1–50 parts (as ammonia) by weight of aqueous ammonia are added thereto with stirring, and then 1–50 parts by weight of hydrogen peroxide in aqueous solution are added dropwise. In place of hydrogen peroxide, ozone and other oxidizing agents such as nitrogen tetroxide, organic peroxides etc. can be used. The solution thus obtained is heated up to 90° C. for 30 minutes with stirring, then the solvent is evaporated, leaving a solid residue. The solid is dried at 130° C., then finally ground and after compression molding, heated at 300°–500° C. for 0.5–24 hours in contact with circulating air.

Having generally described this invention, a further understanding can be obtained by reference to certain specific examples which are provided herein for purposes of illustration only and are not intended to be limiting unless otherwise specified. All parts referred to in these examples are parts by weight.

In the following examples and control examples, the evaluation of the catalysts was conducted under the following conditions unless otherwise stated. A given amount of catalyst was put into a reactor and then a gas mixture of 5% methacrolein, 10% oxygen, 30% steam and 55% nitrogen (by volume, respectively) was passed through the reactor at a given temperature and a space velocity of 2000 l/hr.

EXAMPLE 1

Preparation of the Catalyst 42.4 Parts of ammonium paramolybdate was dissolved in 200 parts of water. To this solution, 2.3 parts of 85% phosphoric acid and 18.9 parts of 60% arsenic acid solution were added. To the slurry thus obtained, 11.7 parts of ammonium metavanadate and 10.1 parts of potassium nitrate were added. The solution was then concentrated with stirring and evaporated to dryness. The solid thus obtained was dried at 130° C. for 16 hours, then finely ground and, after compression molding, calcined at 400° C. for 5 hours in circulating air. The atomic ratio of the metal elements in this catalyst was $P_1Mo_{12}K_{0.5}As_{0.4}V_{0.5}$. We describe this catayst as a highly active catalyst.

The continuous oxidation of methacrolein was then carried out by the above procedure. The data describing the initial performance of the catalyst are shown in Table 1.

While the oxidation reaction continued, the temperature was deliberately increased to provide the abnormal reaction whereby the catalyst became deactivated. The performance data for the deactivated catalyst are also shown in Table 1. The deactivated catalyst was then regenerated by the following procedure.

Regeneration of the deactivated Catalyst

50 Parts of deactivated catalyst and 2.45 parts of ammonium nitrate were added to 100 parts of water, then 75 parts of 28% aqueous ammonia were added thereto, and 5 parts of 35% hydrogen peroxide solution were slowly added dropwise. The solution thus obtained was kept at 90° C. for 30 minutes, then concentrated with stirring and evaporated to dryness. The solid thus obtained was dried at 130° C. for 16 hours, then finely ground and, after compression molding, calcined at 400° C. for 5 hours in circulating air. We describe this catalyst as a regenerated one.

The regenerated catalyst was then evaluated by the above procedure. The performance data for the regenerated catalyst are also shown in Table 1.

From the table it can be seen that the deactivated catalyst has been completely regenerated and is equivalent to the original highly active catalyst.

TABLE 1

| Catalyst | Reaction Temp. (°C.) | Conversion to Methacrolein (%) | Selectivity for Methacrylic acid (%) |
|---|---|---|---|
| highly active catalyst | 285 | 66.0 | 88.0 |
| deactivated catalyst | 330 | 30.3 | 71.5 |
| regenerated catalyst | 285 | 65.1 | 88.1 |

EXAMPLE 2

The deactivated catalyst of Example 1 above was regenerated under the same conditions as in Example 1 except that in place of the hydrogen peroxide solution ozone was passed into the solution at the rate of 25 cc/min for one hour. The data for the catalyst thus regenerated were: 285° C. reaction temperature, 64.8% conversion to methacrolein and 87.8 selectivity for methacrylic acid.

EXAMPLE 3

The deactivated catalyst of Example 1 was regenerated under the same conditions as in Example 1 except that 3.21 parts of 60% of nitric acid was used in place of the ammonium nitrate. The data for the catalyst thus regenerated were: 285° C. reaction temperature, 66.9% conversion to methacrolein and 87.1% selectivity for methacrylic acid.

EXAMPLE 4

The deactivated catalyst of Example 1 above was regenerated under the same conditions as in Example 1 except that 0.5 parts of ammonium nitrate was added to the 100 parts of pure water and then 9 parts of 28% aqueous ammonia were added. The deactivated catalyst did not dissolve in this treatment solution, but its regeneration was not hindered. The data for the catalyst thus regenerated were: 285° C. reaction temperature, 65.0% conversion to methacrolein and 88.0% selectivity for methacrylic acid.

EXAMPLE 5

The highly active catalyst prepared in Example 1 above was deactivated by heating it at 600° C. for 10 hours. The deactivated catalyst was regenerated by the same method as in Example 1. The data for the deactivated catalyst and regenerated catalyst are shown in Table 2.

Table 2

| Catalyst | Reaction Temp. | Conversion to Methacrolein | Selectivity for Methacrylic acid (%) |
|---|---|---|---|
| deactivated catalyst | 330 | 12.5 | 51.4 |
| regenerated catalyst | 290 | 63.5 | 87.0 |

EXAMPLE 6

The same regenerating treatment as in Example 1 was carried out except that no ammonium nitrate was added. The reaction results of the catalyst thus regenerated were 295° C. in reaction temperature, 60.5% conversion of methacrolein and 87.4% selectivity for methacrylic acid.

EXAMPLE 7

In accordance with Example 1 above, the following catalysts were prepared, then intentionally deactivated by heating them at 600° C. for 10 hours, and then regenerated by the same method as in Example 1. The data for these catalysts are shown in Table 3.

Table 3

| Catalyst Composition (atomic ratio) | | Reaction Temp. (°C.) | Conversion to Methacrolein(%) | Selectivity for Methacrylic acid(%) |
|---|---|---|---|---|
| $P_1Mo_{12}Cs_{0.5}$ $As_{0.4}V_{0.5}$ | highly active | 290 | 62.4 | 86.3 |
| | deactivated catalyst | 330 | 15.1 | 50.1 |
| | regenerated catalyst | 295 | 62.0 | 87.4 |
| $P_1Mo_{12}K_1$ $As_{0.5}Cu_{0.5}$ | highly active catalyst | 290 | 63.1 | 86.3 |
| | deactivated catalyst | 330 | 12.0 | 48.5 |
| | regenerated catalyst | 290 | 61.1 | 86.4 |

EXAMPLE 8

In accordance with Example 1 above, a catalyst having the composition shown in Table 4 was prepared. This time, however, the catalyst was calcined at 450° C. for 2 hours. The catalyst was inactivated in the initial stage of methacrolein oxidation reaction by the abnormal reaction caused by intentionally raising the reaction temperature (deactivated catalyst). The catalyst was then regenerated in accordance with Example 1 (regenerated catalyst). The data for these catalyst are shown in Table 4.

Table 4

| Catalyst Composition (atomic ratio) | | Reaction Temp.(°C.) | Conversion to Methacrolein(%) | Selectivity for Methacrylic acid (%) |
|---|---|---|---|---|
| $P_2Mo_{12}Cs_2$ $Mg_2Cu_{0.1}V_{0.5}$ $Cr_{0.5}$ | highly active catalyst | 290 | 60.1 | 86.0 |
| | deactivated catalyst | 350 | 24.1 | 61.4 |
| | Regenerated catalyst | 290 | 58.7 | 85.7 |

CONTROL EXAMPLE 1

The deactivated catalyst of Example above was regenerated under the same conditions as in Example 1 but without using hydrogen peroxide.

CONTROL EXAMPLE 2

Regeneration was conducted under the same conditions as in Example 2 above except that air was used in place of ozone at the rate of 1 l/hr for 2 hours.

EXAMPLE 3

The deactivated catalyst of Example 1 above was regenerated under the same conditions as in Example 1 except that ammonium nitrate and hydrogen peroxide were not used. The data for the regenerated catalysts of control Examples 1, 2 and 3 are shown in Table 5.

Table 5

| Catalyst | Reaction Temp. (°C.) | Conversion to Methacrolein (%) | Selectivity for Methacrylic acid (%) |
|---|---|---|---|
| regenerated cata. of control Ex. 1 | 320 | 47.3 | 78.4 |
| regenerated cata. of control Ex. 2 | 320 | 50.4 | 75.0 |
| regenerated cata. of control Ex. 3 | 330 | 39.7 | 75.0 |
| regenerated cata. of Example 1 | 285 | 66.0 | 88.0 |

The above results show that the catalysts regenerated by treatment with aqueous ammonium nitrate solution alone, aqueous ammonia alone or with aqueous ammonia and air are inferior to the catalyst regenerated by the method of the present invention in their degree of regeneration.

Having fully described the invention, it will be apparent to one of ordinary skill in the art that many changes and modifications can be made thereto without departing from the spirit or scope of the invention as set forth herein.

What is claimed as new and intended to be covered by Letters Patent is:

1. A method for regenerating a deactivated oxidation catalyst comprising phosphorus, molybdenum and an alkali metal deactivated by the gas phase oxidation of an unsaturated aldehyde to an unsaturated carboxylic acid, which comprises:

treating said deactivated catalyst with an aqueous solution containing ammonia and an oxidizing agent selected from the group consisting of hydrogen peroxide and ozone;

removing said solution from said treated catalyst; and drying the separated catalyst.

2. The method of claim 1 wherein said catalyst contains at least one additional element selected from the group consisting of AS, SB, CD, In, Sn, Tl, Ca, V, U, Ce, W, Ni, Zr, Ca, Ba, Fe, Rh, Mn, Re, Ru, Co, Cu, Al, Si, Cr, Ge, Ti, Nb, Ta, Pb, Zn, Sr, Mg, Ca, Pd, B, Bi, Te and Ag.

3. The method of claim 2 wherein said additional element is selected from the group consisting of As, V, W, Cu, Fe, Mn, Sn, Sb, Mg, Ca, Sr, Ba, Si, Co, Zn, Nb, Cr and Bi.

4. The method of claim 1 wherein said aqueous solution contains 1–50 parts by weight of ammonia and 1–50 parts by weight of hydrogen peroxide per 100 parts by weight of deactivated catalyst to be treated.

5. The method of claim 1 wherein said aqueous solution also contains a source of nitrate ions.

6. The method of claim 5, wherein said source of nitrate ions is selected from the group consisting of nitric acid and ammonium nitrate.

7. A method for regenerating a deactivated oxidation catalyst comprising phosphorus, molybdenum, and an alkali metal deactivated by the gas phase oxidation of an unsaturated aldehyde to an unsaturated carboxylic acid, which comprises:

treating said deactivated catalyst with an aqueous solution containing ammonia and an oxidizing agent selected from the group consisting of hydrogen, peroxide, ozone, nitrogen tetraoxide and organic peroxides;

removing said solution from said treated catalyst; and drying the separated catalyst.

* * * * *